United States Patent [19]

Ruoslahti et al.

[11] Patent Number: 5,955,572
[45] Date of Patent: *Sep. 21, 1999

[54] STRUCTURAL MIMICS OF RGD-BINDING SITES

[75] Inventors: Erkki Ruoslahti, Rancho Sante Fe; Renata Pasqualini, Solana Beach, both of Calif.

[73] Assignee: La Jolla Cancer Research Foundation, La Jolla, Calif.

[*] Notice: This patent is subject to a terminal disclaimer.

[21] Appl. No.: 09/079,432

[22] Filed: May 14, 1998

Related U.S. Application Data

[63] Continuation of application No. 08/520,535, Aug. 28, 1995, Pat. No. 5,817,750.

[51] Int. Cl.$^6$ ................................. C07K 7/06; C07K 7/64
[52] U.S. Cl. ................................. 530/317; 514/9; 514/11
[58] Field of Search ................................. 530/317; 514/9, 514/11

[56] References Cited

U.S. PATENT DOCUMENTS

| | | |
|---|---|---|
| 5,149,780 | 9/1992 | Plow et al. . |
| 5,192,746 | 3/1993 | Lobl et al. . |
| 5,204,445 | 4/1993 | Plow et al. . |
| 5,536,814 | 7/1996 | Ruoslahti et al. . |

FOREIGN PATENT DOCUMENTS

| | | |
|---|---|---|
| 578 083 | 1/1994 | European Pat. Off. . |
| WO90/03983 | 4/1990 | WIPO . |
| WO91/07977 | 6/1991 | WIPO . |

OTHER PUBLICATIONS

McMurray et al., *Tetrahedron Letters*, 34:8059–8062 (1993).

Pasqualini et al., "A Peptide Isolated from Phage Display Libraries Is a Structural and Functional Mimic of an RGD–binding Site on Integrins," *J. Cell Biol.* 130:1189–1196 (1995).

Pasqualini et al., "Determination of the Putative Binding Site for Fibronectin on Platelet Glycoprotein IIb–IIIa Complex through a Hydropathic Complementarity Approach," *J. Biol. Chem.* 264:14566–14570 (1989).

Pierschbacher et al., "Influence of Stereochemistry of the Sequence Arg–Gly–Asp–Xaa on Binding Specificity in Cell Adhesion," *J. Biol. Chem.* 262:17294–17298 (1987).

Pfaff et al., "Comparison of Disintegrins with Limited Variation in the RGD Loop in Their Binding to Purified Integrins αIIbβ3, αvβ3 and α5β1 and in Cell Adhesion Inhibition,"*Cell Adhesion and Communication* 2:491–501 (1994).

Smith and Cheresh, "Integrin ($\alpha_v\beta_3$)–Ligand Interaction," *J. Biol. Chem.* 265:2168–2172 (1990).

Smith and Cheresh, "The Arg–Gly–Asp Binding Domain of the Vitronectin Receptor," *J. Biol. Chem.* 263:18726–18731 (1988).

Steiner et al., "$Ca^{2+}$–dependent Binding of a Synthetic Arg–Gly–Asp (RGD) Peptide to a Single Site on the Purified Platelet Glycoprotein Iib–IIIa Complex," *J. Biol. Chem.* 264:13102–13108 (1989).

Takada et al., "A Point Mutation of Integrin $\beta_1$ Subunit Blocks Binding of $\alpha_5\beta_1$ to Fibronectin and Invasin but not Recruitment to Adhesion Plaques," *J. Cell Biol.* 119:913–921 (1992).

Cierniewski et al., "Characterization of Cation–Binding Sequences in the Platelet Integrin GPIIb–IIIa ($_{IIb}\beta_3$) by Terbium Luminescence," *Biochemistry* 33:12238–12246 (1994).

D'Souza et al., "Ligand and Cation Binding Are Dual Functions of a Discrete Segment of the Integrin $\beta_3$ Subunit: Cation Displacement Is Involved in Ligand Binding," *Cell* 79:659–667 (1994).

D'Souza et al., "Localization of an Arg–Gly–Asp Recognition Site Within an Integrin Adhesion Receptor," *Science* 242:91–93 (1988).

D'Souza et al., "Chemical Cross–linking of Arginyl–Glycyl–Aspartic Acid Peptides to an Adhesion Receptor of Platelets," *J. Biol. Chem.* 263: 3943–3951 (1988).

Edgington, "How Sweet It Is: Selectin–Mediating Drugs," *Bio/Technology* 10:383–389 (1992).

Ginsberg et al., "Divalent Cation Regulation of the Surface Orientation of Platelet Membrane Glycoprotein IIb,"*J. Clin. Invest.* 78:1103–1111 (1986).

Haas and Plow, "Integrin–ligand interactions: A Year in Review," *Curr. Opin. in Cell Biol.*, 6:656–662 (1994).

Hynes, "Integrins: Versatility, Modulation, and Signaling in Cell Adhesion," *Cell* 69:11–25 (1992).

Koivunen et al., "Phage Libraries Displaying Cyclic Peptides with Different Ring Sizes: Ligand Specificities of the RGD Directed Integrins," *Bio/Technology* 13:265–270 (1995).

Loftus et al., "A $\beta_3$ Integrin Mutation Abolished Ligand Binding and Alters Divalent Cation–Dependent Conformation," *Science* 249:915–918 (1990).

Marder, "Ligand Interactions with the RGD Recognition Site Alter Binding of GPIIb–IIIa Reactive Monoclonal Antibody to Human Platelets," *Biochem. Biophys. Res. Comm.* 195(2):799–806 (1993).

Bajt and Loftus, "Mutation of a Ligand Binding Domain of $\beta_3$ Integrin," *J. Biol. Chem.* 269: 20913–20919 (1994).

(List continued on next page.)

*Primary Examiner*—Cecilia J. Tsang
*Attorney, Agent, or Firm*—Campbell & Flores

[57] ABSTRACT

The present invention provides cyclic peptides that recognize the arginine-glycine-aspartic acid (RGD) motif characteristic of many integrin ligands. These cyclic RGD-binding peptides, which comprise the motif (W/P)DD(G/L)(W/L)(W/L/M), have a structure that functionally mimics the RGD-binding site on an integrin. The invention further provides an antibody selectively reactive with a cyclic RGD-binding peptide containing the sequence (W/P)DD(G/L)(W/L)(W/L/M). The invention also provides a method to reduce or inhibit cell attachment to an RGD-containing ligand using a cyclic RGD-binding peptide of the invention.

21 Claims, 1 Drawing Sheet

OTHER PUBLICATIONS

Bajt et al., "A Spontaneous Mutation of Integrin $\alpha_{IIb}\beta_3$ (Platelet Glycoprotein IIb–IIIa) Helps Define a Ligand Binding Site," *J. Biol. Chem.* 267: 3789–3794 (1992).

Calvete et al., "Proteolytic degradation of the RGD–binding and non–RGD–binding conformers of human platelet integrin glycoprotein IIb/IIIa: clues for identification of regions involved in the receptor's activation," *Biochem. J.* 298:1–7 (1994).

Charo et al., "Inhibition of Fibrinogen Binding to GP IIb–IIIa by a GP IIIa Peptide," *J. Biol. Chem.* 266: 1415–1421 (1991).

Tuckwell et al., "Homology Modelling of Integrin EF–hands," *Biochem. J.* 285:325–331 (1992).

Vezenkov, "Peptides Containing the Arg–Gly–Asp Sequence as Inhibitiors of Platelet Aggregation: A Review," *Bulg. Chem. Commun.* 26:292–300 (1993).

Wood and Wetzel, "Novel cyclization chemistry especially suited for biologically derived, unprotected peptides," *Int J. Peptide Protein Res.* 39:533–539 (1992).

5,955,572

SEQUENCE LISTING (1) GENERAL INFORMATION:

(iii) NUMBER OF SEQUENCES: 28

(2) INFORMATION FOR SEQ ID NO:1:

```
    (i) SEQUENCE CHARACTERISTICS:
         (A) LENGTH: 8 amino acids
         (B) TYPE: amino acid
         (D) TOPOLOGY: circular (xi) SEQUENCE DESCRIPTION: SEQ ID NO:1:

Cys Trp Asp Asp Gly Trp Leu Cys
1               5

(2) INFORMATION FOR SEQ ID NO:2:

(i) SEQUENCE CHARACTERISTICS:
         (A) LENGTH: 9 amino acids
         (B) TYPE: amino acid
         (D) TOPOLOGY: circular (xi) SEQUENCE DESCRIPTION: SEQ ID NO:2:

Cys Trp Asp Asp Leu Trp Trp Leu Cys
1               5

(2) INFORMATION FOR SEQ ID NO:3:

(i) SEQUENCE CHARACTERISTICS:
         (A) LENGTH: 8 amino acids
         (B) TYPE: amino acid
         (D) TOPOLOGY: circular (xi) SEQUENCE DESCRIPTION: SEQ ID NO:3:

Cys Trp Asp Asp Gly Leu Met Cys
1               5

(2) INFORMATION FOR SEQ ID NO:4:

(i) SEQUENCE CHARACTERISTICS:
         (A) LENGTH: 8 amino acids
         (B) TYPE: amino acid
         (D) TOPOLOGY: circular (xi) SEQUENCE DESCRIPTION: SEQ ID NO:4:

Cys Trp Asp Asp Gly Trp Met Cys
1               5

(2) INFORMATION FOR SEQ ID NO:5:

(i) SEQUENCE CHARACTERISTICS:
         (A) LENGTH: 10 amino acids
         (B) TYPE: amino acid
         (D) TOPOLOGY: circular (xi) SEQUENCE DESCRIPTION: SEQ ID NO:5:

Cys Leu Val Trp Leu Leu Val Gln Phe Tyr
1               5                  10

(2) INFORMATION FOR SEQ ID NO:6:

(i) SEQUENCE CHARACTERISTICS:
         (A) LENGTH: 10 amino acids
         (B) TYPE: amino acid
         (D) TOPOLOGY: circular (xi) SEQUENCE DESCRIPTION: SEQ ID NO:6:

Cys Thr Phe Gly Gly Gly Ile Gly Arg Val
1               5                  10

(2) INFORMATION FOR SEQ ID NO:7:

(i) SEQUENCE CHARACTERISTICS:
```

(A) LENGTH: 9 amino acids
        (B) TYPE: amino acid
        (D) TOPOLOGY: circular (xi) SEQUENCE DESCRIPTION: SEQ ID NO:7:

Cys Thr Leu Arg Phe Gln Arg Ser Cys
1               5

(2) INFORMATION FOR SEQ ID NO:8:

(i) SEQUENCE CHARACTERISTICS:
        (A) LENGTH: 9 amino acids
        (B) TYPE: amino acid
        (D) TOPOLOGY: circular (xi) SEQUENCE DESCRIPTION: SEQ ID NO:8:

Cys Ser Trp Asp Asp Gly Trp Leu Cys
1               5

(2) INFORMATION FOR SEQ ID NO:9:

(i) SEQUENCE CHARACTERISTICS:
        (A) LENGTH: 9 amino acids
        (B) TYPE: amino acid
        (D) TOPOLOGY: circular (xi) SEQUENCE DESCRIPTION: SEQ ID NO:9:

Cys Pro Asp Asp Leu Trp Trp Leu Cys
1               5

(2) INFORMATION FOR SEQ ID NO:10:

(i) SEQUENCE CHARACTERISTICS:
        (A) LENGTH: 8 amino acids
        (B) TYPE: amino acid
        (D) TOPOLOGY: circular (xi) SEQUENCE DESCRIPTION: SEQ ID NO:10:

Cys Asp Gly Trp Leu Gly Phe Cys
1               5

(2) INFORMATION FOR SEQ ID NO:11:

(i) SEQUENCE CHARACTERISTICS:
        (A) LENGTH: 10 amino acids
        (B) TYPE: amino acid
        (D) TOPOLOGY: circular (xi) SEQUENCE DESCRIPTION: SEQ ID NO:11:

Cys Gln Arg Ile Val Leu Gly Phe Thr Cys
1               5                   10

(2) INFORMATION FOR SEQ ID NO:12:

(i) SEQUENCE CHARACTERISTICS:
        (A) LENGTH: 8 amino acids
        (B) TYPE: amino acid
        (D) TOPOLOGY: circular (xi) SEQUENCE DESCRIPTION: SEQ ID NO:12:

Cys Asp Tyr Trp Leu Gly Phe Cys
1               5

(2) INFORMATION FOR SEQ ID NO:13:

(i) SEQUENCE CHARACTERISTICS:
        (A) LENGTH: 8 amino acids
        (B) TYPE: amino acid (D) TOPOLOGY: circular (xi) SEQUENCE DESCRIPTION: SEQ ID NO:13:

Cys Phe Val Leu Trp Leu Val Cys
1               5

(2) INFORMATION FOR SEQ ID NO:14:

(i) SEQUENCE CHARACTERISTICS:
    (A) LENGTH: 7 amino acids
    (B) TYPE: amino acid
    (D) TOPOLOGY: circular (xi) SEQUENCE DESCRIPTION: SEQ ID NO:14:

Cys Gly Asn Arg Leu Arg Cys
1               5

(2) INFORMATION FOR SEQ ID NO:15:

(i) SEQUENCE CHARACTERISTICS:
    (A) LENGTH: 6 amino acids
    (B) TYPE: amino acid
    (D) TOPOLOGY: linear (xi) SEQUENCE DESCRIPTION: SEQ ID NO:15:

Gly Arg Gly Asp Ser Pro
1               5

(2) INFORMATION FOR SEQ ID NO:16:

(i) SEQUENCE CHARACTERISTICS:
    (A) LENGTH: 9 amino acids
    (B) TYPE: amino acid
    (D) TOPOLOGY: circular (xi) SEQUENCE DESCRIPTION: SEQ ID NO:16:

Cys Glu Leu Arg Gly Asp Gly Trp Cys
1               5

(2) INFORMATION FOR SEQ ID NO:17:

(i) SEQUENCE CHARACTERISTICS:
    (A) LENGTH: 10 amino acids
    (B) TYPE: amino acid
    (D) TOPOLOGY: circular (xi) SEQUENCE DESCRIPTION: SEQ ID NO:17:

Cys Arg Asp Pro Arg Ala Gln Asp Leu Cys
1               5                   10

(2) INFORMATION FOR SEQ ID NO:18:

(i) SEQUENCE CHARACTERISTICS:
    (A) LENGTH: 10 amino acids
    (B) TYPE: amino acid
    (D) TOPOLOGY: circular (xi) SEQUENCE DESCRIPTION: SEQ ID NO:18:

Ala Cys Arg Gly Asp Gly Trp Met Cys Gly
1               5                   10

(2) INFORMATION FOR SEQ ID NO:19:

(i) SEQUENCE CHARACTERISTICS:
    (A) LENGTH: 13 amino acids
    (B) TYPE: amino acid
    (D) TOPOLOGY: circular (xi) SEQUENCE DESCRIPTION: SEQ ID NO:19:

Gly Ala Cys Val Arg Leu Asn Ser Leu Ala Cys Gly Ala
    1               5                   10

(2) INFORMATION FOR SEQ ID NO:20:

(i) SEQUENCE CHARACTERISTICS:
        (A) LENGTH: 8 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa is an independently
            selected amino acid."

(ix) FEATURE:
        (A) NAME/KEY: Peptide
        (B) LOCATION: 2
        (D) OTHER INFORMATION: /note= "Xaa is an amino acid that
            together with the amino acid at position 7 equals
            0 to 4 amino acids, each amino acid of which is
            independently selected."

(ix) FEATURE:
        (A) NAME/KEY: Peptide
        (B) LOCATION: 5
        (D) OTHER INFORMATION: /note= "Xaa is an amino acid
            selected from the group consisting of glycine and
            leucine."

(ix) FEATURE:
        (A) NAME/KEY: Peptide
        (B) LOCATION: 6
        (D) OTHER INFORMATION: /note= "Xaa is an amino acid
            selected from the group consisting of tryptophan
            and leucine."

(ix) FEATURE:
        (A) NAME/KEY: Peptide
        (B) LOCATION: 7
        (D) OTHER INFORMATION: /note= "Xaa is an amino acid that
            together with the amino acid at position 2 equals
            0 to 4 amino acids, each amino acid of which is
            independently selected."

(ix) FEATURE:
        (A) NAME/KEY: Peptide
        (B) LOCATION: 8
        (D) OTHER INFORMATION: /note= "Xaa is an independently
            selected amino acid."

(xi) SEQUENCE DESCRIPTION: SEQ ID NO:20:

Xaa Xaa Asp Asp Xaa Xaa Xaa Xaa
    1               5

(2) INFORMATION FOR SEQ ID NO:21:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:21:

Gly Arg Gly Glu Ser Pro
    1               5

(2) INFORMATION FOR SEQ ID NO:22:

(i) SEQUENCE CHARACTERISTICS:
        (A) LENGTH: 10 amino acids
        (B) TYPE: amino acid
        (D) TOPOLOGY: circular

```
    (ix) FEATURE:
         (A) NAME/KEY: Peptide
         (B) LOCATION: 1
         (D) OTHER INFORMATION: /note= "Xaa is an independently
             selected amino acid."

(ix) FEATURE:
         (A) NAME/KEY: Peptide
         (B) LOCATION: 2
         (D) OTHER INFORMATION: /note= "Xaa is an amino acid that
             together with the amino acid at position 9 equals
             0 to 3 amino acids, each amino acid of which is
             independently selected."

(ix) FEATURE:
         (A) NAME/KEY: Peptide
         (B) LOCATION: 3
         (D) OTHER INFORMATION: /note= "Xaa is an amino acid
             selected from the group consisting of tryptophan
             and proline."

(ix) FEATURE:
         (A) NAME/KEY: Peptide
         (B) LOCATION: 6
         (D) OTHER INFORMATION: /note= "Xaa is an amino acid
             selected from the group consisting of glycine and
             leucine."

(ix) FEATURE:
         (A) NAME/KEY: Peptide
         (B) LOCATION: 7
         (D) OTHER INFORMATION: /note= "Xaa is an amino acid
             selected from the group consisting of tryptophan
             and leucine."

(ix) FEATURE:
         (A) NAME/KEY: Peptide
         (B) LOCATION: 8
         (D) OTHER INFORMATION: /note= "Xaa is an amino acid
             selected from the group consisting of leucine,
             tryptophan and methionine."

(ix) FEATURE:
         (A) NAME/KEY: Peptide
         (B) LOCATION: 9
         (D) OTHER INFORMATION: /note= "Xaa is an amino acid that
             together with the amino acid at position 2 equals
             0 to 3 amino acids, each amino acid of which is
             independently selected."

(ix) FEATURE:
         (A) NAME/KEY: Peptide
         (B) LOCATION: 10
         (D) OTHER INFORMATION: /note= "Xaa is an independently
             selected amino acid"

(xi) SEQUENCE DESCRIPTION: SEQ ID NO:22:

Xaa Xaa Xaa Asp Asp Xaa Xaa Xaa Xaa Xaa
1               5                   10

(2) INFORMATION FOR SEQ ID NO:23:

(i) SEQUENCE CHARACTERISTICS:
        (A) LENGTH: 25 amino acids
        (B) TYPE: amino acid
        (D) TOPOLOGY: linear (xi) SEQUENCE DESCRIPTION: SEQ ID NO:23:

Asp Tyr Pro Val Asp Ile Tyr Tyr Leu Met Asp Leu Ser Tyr Ser Met
1               5                   10                  15

Lys Asp Asp Leu Trp Ser Ile Gln Asn
                20                  25

(2) INFORMATION FOR SEQ ID NO:24:
```

(i) SEQUENCE CHARACTERISTICS:
        (A) LENGTH: 25 amino acids
        (B) TYPE: amino acid
        (D) TOPOLOGY: linear (xi) SEQUENCE DESCRIPTION: SEQ ID NO:24:

Asp Tyr Pro Val Asp Ile Tyr Tyr Leu Met Asp Leu Ser Tyr Ser Met
1               5                   10                  15

Lys Ala Ala Leu Trp Ser Ile Gln Asn
            20                  25

(2) INFORMATION FOR SEQ ID NO:25:

(i) SEQUENCE CHARACTERISTICS:
        (A) LENGTH: 28 amino acids
        (B) TYPE: amino acid
        (D) TOPOLOGY: linear (xi) SEQUENCE DESCRIPTION: SEQ ID NO:25:

Asp Ile Tyr Tyr Leu Met Asp Leu Ser Tyr Ser Met Lys Asp Asp Leu
1               5                   10                  15

Trp Ser Ile Gln Asn Leu Gly Thr Lys Leu Ala Thr
            20                  25

(2) INFORMATION FOR SEQ ID NO:26:

(i) SEQUENCE CHARACTERISTICS:
        (A) LENGTH: 28 amino acids
        (B) TYPE: amino acid
        (D) TOPOLOGY: linear (xi) SEQUENCE DESCRIPTION: SEQ ID NO:26:

Asp Leu Tyr Tyr Leu Met Asp Leu Ser Tyr Ser Met Lys Asp Asp Leu
1               5                   10                  15

Glu Asn Val Lys Ser Leu Gly Thr Asp Leu Met Asn
            20                  25

(2) INFORMATION FOR SEQ ID NO:27:

(i) SEQUENCE CHARACTERISTICS:
        (A) LENGTH: 29 amino acids
        (B) TYPE: amino acid
        (D) TOPOLOGY: linear (xi) SEQUENCE DESCRIPTION: SEQ ID NO:27:

Asp Leu Tyr Tyr Leu Met Asp Leu Ser Leu Ser Met Lys Asp Asp Leu
1               5                   10                  15

Asp Asn Ile Arg Ser Leu Gly Thr Lys Leu Ala Glu Glu
            20                  25

(2) INFORMATION FOR SEQ ID NO:28:

(i) SEQUENCE CHARACTERISTICS:
        (A) LENGTH: 29 amino acids
        (B) TYPE: amino acid
        (D) TOPOLOGY: linear (xi) SEQUENCE DESCRIPTION: SEQ ID NO:28:

Asp Leu Tyr Tyr Leu Met Asp Leu Ser Ala Ala Met Asp Asp Asp Leu
1               5                   10                  15

Asn Thr Ile Lys Glu Leu Gly Ser Gly Leu Ser Lys Glu
            20                  25

STRUCTURAL MIMICS OF RGD-BINDING SITES

This application is a continuation of application U.S. Ser. No. 08/520,535, filed Aug. 28, 1995, U.S. Pat. No. 5,817,750.

This invention was made with government support under grants CA62042, CA28896, and Cancer Center Support grant CA30199 awarded by the National Cancer Institute. The government has certain rights in the invention.

BACKGROUND OF THE INVENTION

1. Field of the Invention

This invention relates generally to the field of cell adhesion and more specifically to integrins and their RGD-binding domains.

2. Background Information

Many cell-cell and cell-matrix interactions depend upon the engagement of specific ligands by members of the integrin family of cell-adhesion receptors. Integrins are heterodimeric transmembrane receptors whose ligand-binding specificity is determined by the combination of α and β subunits. Of associations between the nine known β subunits and 17 known α subunits, integrins $α_5β_1$, $α_{IIb}β_3$ and all or most $α_v$-containing integrins, but generally not others, recognize an arginine-glycine-aspartic acid (RGD) motif. Ligands for these RGD-binding integrins include a variety of extracellular matrix proteins such as fibronectin, vitronectin, osteopontin and collagens; plasma proteins such as fibrinogen and von Willebrand factor; cellular counter-receptors; the disintegrins; and viral proteins.

Integrins are fundamental to processes of physical adhesion involving cell-cell or cell-matrix interactions and also can mediate signal transduction through their cytoplasmic domains. RGD-binding integrins function in biological processes including cell migration in development, wound healing and tissue repair, platelet aggregation and immune cell recognition. A role for these integrins also is implicated in a variety of pathologies including thrombosis, osteoporosis, tumor growth and metastasis, inflammation and diseases of viral etiology such as acquired immune deficiency syndrome. The physiological relevance of integrins is underscored by the observation that hereditary mutations can destroy RGD-binding activity and have pathological consequences resulting in, for example, the bleeding disorder, Glanzmann's thrombasthenia.

Peptides and protein fragments can be used to modulate the activities of RGD-binding integrins. One class of peptides that can act as competitors of RGD-binding activity includes peptides that contain the RGD motif or a functional equivalent of this motif. A second class of peptides includes those peptides that bind RGD-containing ligands through structures that function similarly to the integrin domain that contacts the RGD sequence. Peptides that structurally mimic the RGD-binding site in integrin β subunits, for example, can modulate the activity of RGD-binding integrins.

Peptides that specifically bind ligands of RGD-binding integrins would be useful for modulating the cell aggregation and cell adhesion that occur in various pathological conditions including, for example, thrombosis, osteoporosis, inflammation, metastasis, wound healing and graft rejection. However, few such peptides have been described. Thus, there is a need for peptides that effectively and selectively modulate the activity of RGD-binding integrins. The present invention satisfies this need by providing novel cyclic peptides having specific RGD-binding activity and provides related advantages as well.

SUMMARY OF THE INVENTION

The present invention provides cyclic peptides that recognize the arginine-glycine-aspartic acid (RGD) motif characteristic of many integrin ligands. These cyclic RGD-binding peptides, which comprise the motif (W/P)DD(G/L)(W/L)(W/L/M), have a structure that functionally mimics the RGD-binding site on an integrin. The invention further provides an antibody selectively reactive with a cyclic RGD-binding peptide containing the sequence (W/P)DD(G/L)(W/L)(W/L/M). The invention also provides a method to reduce or inhibit cell attachment to an RGD-containing ligand using a cyclic RGD-binding peptide of the invention.

DETAILED DESCRIPTION OF THE INVENTION

Figure 1A:
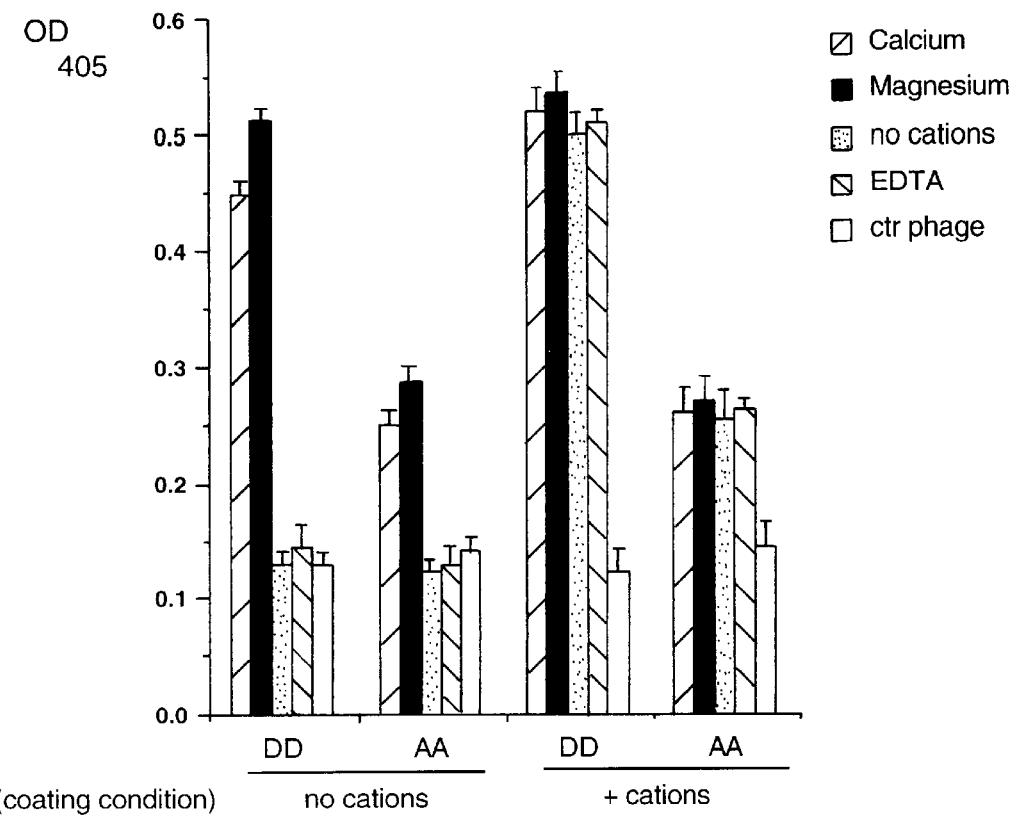
FIG. 1 shows binding of RGD-displaying phage to peptides from the β3 integrin subunit. (a) Synthetic peptides DYPVDIYYLMDLSYSMKDDLWSIQN (SEQ. ID. NO. 23), designated "DD," and DYPVDIYYLMDLSYSMKAALWSIQN (SEQ. ID. NO. 24), designated "AA," were coated at 100 μg/ml onto microtiter wells in the presence or absence of 1 mM divalent cations. CELRGDGWC-phage (SEQ. ID. NO. 16) were incubated in the presence or absence of EDTA (10 mM) or calcium or magnesium (1 mM). Antibodies against M13 phage were used to quantify the amount of bound phage. Phage displaying an unrelated peptide sequence, CRDPRAODLC (SEQ. ID. NO. 17), were tested as control phage. ▨, Calcium; ■, magnesium; ▧, no cations; □, control phage. (b) The effect of soluble GRGDSP (SEQ. ID. NO. 15) or CWDDGWLC (SEQ. ID. NO. 1) peptides on the binding of phage to the same integrin peptides as in a was analyzed. The data in a and b represent the mean values from triplicate wells with standard error less than 10% of the mean ■, Magnesium; ▨, CWDDGWLC (SEQ. ID. NO. 1); ▧, GRGDSP (SEQ. ID. NO. 15); □, control phage.

The present invention provides cyclic peptides that recognize the arginine-glycine-aspartic acid (RGD) motif characteristic of many integrin ligands. These cyclic RGD-binding peptides, which comprise the motif (W/P)DD(G/L)(W/L)(W/L/M), have a structure that functionally mimics the RGD-binding site on an integrin. Peptides of the present invention are distinguished by RGD-binding activity. The RGD-binding activity of the peptides is further characterized as divalent cation independent. Cyclic peptides that have RGD-binding activity include, for example, the peptides CWDDGWLC (SEQ. ID. NO. 1) and CWDDLWWLC (SEQ. ID. NO. 2) as well as other peptides having the consensus sequence (W/P)DD(G/L)(W/L)(W/L/M) shown in Table 2 below. As used herein, underlining of peptide sequences indicates that the structure of the peptide is cyclic.

As used herein, the term "peptide" refers to linear or cyclic or branched compounds containing amino acids, amino acid equivalents or other non-amino groups, while still retaining the desired functional activity of a peptide. Peptide equivalents can differ from conventional peptides by the replacement of one or more amino acids with related organic acids such as p-aminobenzoic acid (PABA), amino acid analogs, or the substitution or modification of side chains or functional groups. Peptide equivalents encompass peptide mimetics or peptidomimetics, which are organic molecules that retain similar peptide chain pharmacophore groups as are present in the corresponding peptide. The term "peptide" refers to peptide equivalents as well as peptides.

It is to be understood that limited modifications can be made to a peptide without destroying its biological function. Thus, modifications of the peptides of the present invention that do not completely destroy their RGD-binding activity are within the definition of the compound claims as such. Modifications can include, for example, additions, deletions, or substitutions of amino acid residues; substitutions of compounds that mimic amino acid structure or function; as well as the addition of chemical moieties such as amino or acetyl groups.

As used herein, the term "cyclic peptide" refers to a peptide having an intramolecular bond between two non-adjacent amino acids. The cyclization can be effected through a covalent or non-covalent bond. Intramolecular bonds include, but are not limited to, backbone to backbone, side-chain to backbone and side-chain to side-chain bonds. A preferred method of cyclizing peptides of the present invention is through formation of a disulfide bond between the side-chains of amino acids $X_1$ and $X_8$. Residues capable of forming a disulfide bond include cysteine (Cys), penicillamine (Pen), β,β-pentamethylene cysteine (Pmc), β,β-pentamethylene-β-mercaptopropionic acid (Pmp) and functional equivalents thereof (see Table 1).

The peptides disclosed herein also can cyclize, for example, via a lactam bond, which can utilize a side-chain group of $X_8$ to form a covalent attachment to the N-terminal amine of $X_1$. Residues capable of forming a lactam bond include aspartic acid (Asp), glutamic acid (Glu), lysine (Lys), ornithine (Orn), α,β-diaminopropionic acid, γ-aminoadipic acid (Adp) and M-(aminomethyl)benzoic acid (Mamb). In particular, $X_8$ in a lactam-bonded peptide can be an aspartic acid or glutamic acid residue. Cyclization additionally can be

TABLE 1

AMINO ACIDS AND AMINO ACID ANALOGS USEFUL FOR EFFECTIVE CYCLIZATION

| AMINO ACID* | THREE LETTER CODE | TYPE OF BOND |
| --- | --- | --- |
| γ-amino-adipic acid | Adp | Lactam |
| Aspartic acid | Asp | Lactam |
| Cysteine | Cys | Disulfide |
| Glutamic acid | Glu | Lactam |
| Leucine | Leu | Lysinonorleucine |
| Lysine | Lys | Lactam and Lysinonorleucine |
| M-(aminomethyl) benzoic acid | Mamb | Lactam |
| Ornithine | Orn | Lactam |
| Penicillamine | Pen | Disulfide |
| α,β-diaminopropionic acid | — | Lactam |
| β,β-pentamethylene cysteine | Pmc | Disulfide |
| β,β-pentamethylene-β-mercaptopropionic acid | Pmp | Disulfide |
| Tyrosine | Tyr | Dityrosine |

*- includes amino acids and analogs thereof.

effected, for example, through the formation of a lysinonorleucine bond between lysine (Lys) and leucine (Leu) residues or a dityrosine bond between two tyrosine (Tyr) residues.

As used herein, the term "RGD-binding activity" refers to an interaction with a ligand containing an arginine-glycine-aspartic acid (RGD) sequence, or a functional or structural equivalent of this sequence, such that the interaction is specific or selective. Thus, naturally occurring RGD-binding sites in integrin β subunits, as well as structural mimics of RGD-binding sites, are characterized by having RGD-binding activity.

RGD-containing ligands can be proteins, polypeptides or peptides. Thus, RGD-binding activity refers to the binding of RGD-containing proteins, or fragments thereof, such as vitronectin, fibronectin or fibrinogen, as well as to the binding of RGD-containing peptides or their functional equivalents. RGD-binding activity is to be distinguished from non-specific binding activity, such as non-specific adsorption to a surface or to a peptide unrelated in sequence to the arginine-glycine-aspartic acid motif. Specific or selective binding can readily be distinguished from non-specific binding by including the appropriate controls in a binding assay. Several methods for determining RGD-binding activity are described in Example II.

A distinctive characteristic of such RGD-binding activity is that the interaction between the RGD-binding domain and the RGD-containing ligand can be disrupted or prevented by addition of specific competitive sequences. For example, the binding of phage displaying peptides having RGD-binding activity to fibronectin fragments can be blocked by addition of synthetic peptides encoding RGD or by peptides containing an RGD-binding site, such as the peptides CWDDGWLC (SEQ. ID. NO. 1) or CWDDLWWLC (SEQ. ID. NO. 2).

As used herein, the term "RGD-containing ligand" encompasses proteins, polypeptides and peptides having at least one arginine-glycine-aspartic acid sequence, or functional equivalent of an arginine-glycine-aspartic acid sequence, which can function as a ligand for an integrin type receptor. Integrin receptors can bind a variety of RGD-containing peptides (Ruoslahti et al., In *Morphoregulatory Molecules* (Edelman et al., 1990); Ruoslahti et al., *J. Clin. Invest.* 87: 1–5 (1991)).

The term RGD-containing ligand encompasses proteins or peptides which are functional equivalents of RGD-containing ligands. The term "functional equivalent" in reference to an RGD-containing ligand means a ligand having the same or similar activity as an RGD-containing ligand. A functional equivalent of an RGD-containing ligand can, for example, compete for binding to the integrin $\alpha_{IIb}\beta_3$. RGD-containing ligands include ligands containing amino acid equivalents of arginine, such as lysine or homoarginine (homoArg), in place of arginine. Similarly, RGD-containing ligands may contain amino acid equivalents of glycine or aspartic acid in place of glycine or aspartic acid, respectively.

As used herein, the term "amino acid equivalents" refers to compounds which depart from the structure of naturally occurring amino acids, but which have substantially the structure of an amino acid, such that they can be substituted within a peptide or protein which retains its biological activity. Thus, for example, amino acid equivalents can include amino acids having side chain modifications or substitutions, and also can include related organic acids, amides or the like. Amino acid equivalents include amino acid mimetics, which are those structures which exhibit substantially the same spatial arrangement of functional groups as amino acids but do not necessarily have both the α-amino and α-carboxyl groups characteristic of amino acids. The term "amino acid" refers both to amino acids and amino acid equivalents.

Therefore, a peptide comprising, for example, KGD is considered an RGD-containing ligand within the meaning of the present invention. In addition, the anti-$\alpha_{IIb}\beta_3$ monoclonal antibodies, PAC1, OPG2 and LJ-CP3, which each contain an RYD sequence as a functional equivalent of RGD, further exemplify RGD-containing ligands.

The present invention provides cyclic peptides having RGD-binding activity, comprising the amino acid sequence:

$X_1X_2DDX_4X_5X_7X_8$ (SEQ. ID. NO. 20), wherein $X_1$ and $X_8$ each is an independently selected amino acid; $X_2$ and $X_7$ together equal 0 to 4 amino acids, each of which is independently selected; $X_4$ is selected from the group consisting of glycine and leucine; and $X_5$ is selected from the group consisting of tryptophan and leucine.

Thus, a peptide of the invention (SEQ. ID. NO. 20) contains a cyclic structure which consists of less than 11 amino acids. A peptide of the invention contains two aspartic acid residues followed by a glycine or leucine residue followed by a tryptophan or leucine residue. Therefore, a peptide of the invention includes the consensus motif DD(G/L)(W/L). Furthermore, a peptide of the invention is characterized by having RGD-binding activity, as defined herein. Such peptides are exemplified by CWDDGWLC (SEQ. ID. NO. 1), CWDDLWWLC (SEQ. ID. NO. 2) and CWDDGLMC (SEQ. ID. NO. 3).

In another embodiment, the present invention provides a cyclic peptide having RGD-binding activity, comprising the amino acid sequence:

$X_1X_2X_3DDX_4X_5X_6X_7X_8$ (SEQ. ID. NO. 22), wherein $X_1$ and $X_8$ each is an independently selected amino acid; $X_2$ and $X_7$ together equal 0 to 3 amino acids, each of which is independently selected; $X_3$ is selected from the group consisting of tryptophan and proline; $X_4$ is selected from the group consisting of glycine and leucine; $X_5$ is selected from the group consisting of tryptophan and

TABLE 2

SELECTION OF PEPTIDES FROM PHAGE DISPLAY PEPTIDE LIBRARIES THAT BIND TO FIBRONECTIN TYPE $III_{10}$ RGD-CONTAINING FRAGMENTS

| ELUTION STRATEGY | PEPTIDE SEQUENCE (SEQ. ID. NO.) | NUMBER OF ISOLATES |
|---|---|---|
| RGD ELUTION | CWDDGWLC (SEQ. ID. NO. 1) | 131 |
|  | CWDDLWWLC (SEQ. ID. NO. 2) | 10 |
|  | CWDDGLMC (SEQ. ID. NO. 3) | 7 |
|  | CWDDGWMC (SEQ. ID. NO. 4) | 4 |
| EDTA ELUTION | CWDDGWLC (SEQ. ID. NO. 1) | 21 |
|  | CLVWLLVOFY (SEQ. ID. NO. 5) | 2 |
|  | CTFGGGIGRV (SEQ. ID. NO. 6) | 1 |
|  | CTLRFORSC (SEQ. ID. NO. 7) | 1 |
| DIRECT INFECTION OF WELLS | CWDDGWLC (SEQ. ID. NO. 1) | 45 |
|  | CSWDDGWLC (SEQ. ID. NO. 8) | 6 |
|  | CPDDLWWLC (SEQ. ID. NO. 9) | 3 |
|  | CDGWLGFC (SEQ. ID. NO. 10) | 2 |
|  | CORIVLGFTC (SEQ. ID. NO. 11) | 1 |
|  | CDYWLGFC (SEQ. ID. NO. 12) | 1 |
|  | CFVLWLVC (SEQ. ID. NO. 13) | 1 |
|  | CGNRLRC (SEQ. ID. NO. 14) | 1 |

[a] Peptide sequences displayed by phage isolated by different elution strategies.
[b] The number of phage displaying the same amino acid motif is indicated in parenthesis.

leucine; and $X_6$ is selected from the group consisting of tryptophan, leucine and methionine.

Thus, a peptide of the invention (SEQ. ID. NO. 22) contains a cyclic structure which consists of less than 11 amino acids. A peptide of the invention contains a tryptophan or proline residue followed by two aspartic acid residues followed by a glycine or leucine residue followed by a tryptophan or leucine residue followed by a tryptophan, leucine or methionine residue. Therefore, a peptide of the invention includes the consensus motif (W/P)DD(G/L)(W/L)(W/L/M). Furthermore, a peptide of the invention is characterized by having RGD-binding activity, as defined herein. Examples of such peptides include CWDDGWLC (SEQ. ID. NO. 1), CWDDLWWLC (SEQ. ID. NO. 2) and CWDDGLMC (SEQ. ID. NO. 3).

The present invention further provides cyclic peptides with RGD-binding activity having one of the following sequences: CWDDGWLC (SEQ. ID. NO. 1); CWDDLWWLC (SEQ. ID. NO. 2); CWDDGLMC (SEQ. ID. NO. 3); CWDDGWMC (SEQ. ID. NO. 4); CSWDDGWLC (SEQ. ID. NO. 8); and CPDDLWWLC (SEQ. ID. NO. 9).

The region responsible for RGD-binding activity has been broadly defined within the integrin β subunit. Affinity cross-linking of RGD peptides has suggested that the ligand-binding site in the platelet receptor $\alpha_{IIb}\beta_3$ resides proximal to amino acids 109–171 of the $\beta_3$ subunit. An overlapping region spanning amino acids 61–203 of $\beta_3$ also was implicated in RGD recognition by cross-linking studies with the vitronectin receptor $\alpha_v\beta_3$. In each case, the RGD-binding site is adjacent to or coincident with a site that binds divalent cations, as is discussed further below.

A role for $\beta_3$ amino acids 109–171 in RGD binding is further supported by the high degree of conservation of this region among several integrin β subunits (76% identity at the amino acid level). Within this conserved region, amino acids 109–127 are particularly highly conserved among several β subunits, and it has therefore been suggested that this amino-terminal region is critical to the interaction of integrins with their RGD-containing ligands. A comparison of the highly conserved sequence of $\beta_3$ (SEQ. ID. NO. 25) with the sequences of several other β subunits is shown in Table 3 (see Example IV).

Additional studies with mutant integrins support a role for the conserved $\beta_3$(109–127) region in recognition of RGD-containing ligands. Within this conserved segment, a naturally occurring $\beta_3$ mutation at Asp[119] from a thrombasthenic patient and an analogous mutation in $\beta_1$ disrupt RGD-dependent binding. In addition, RGD-binding is completely absent in Asp[119], Ser[121] or Ser[123] mutants of $\alpha_{IIb}\beta_3$, suggesting that each of these residues is required for integrin binding to RGD-containing ligands. In contrast, mutations at Asp[126], Asp[127] or Ser[130] have relatively minor effects on the RGD-binding of $\alpha_{IIb}\beta_3$. These results suggest that the amino-terminal portion of the conserved $\beta_3$ sequence 109–127 is important for RGD recognition by native integrins.

A peptide containing residues 118–131 of $\beta_3$ retains RGD-binding activity when removed from the context of the intact integrin (D'Souza et al., Cell 79:659–667 (1994)). Furthermore, residues 118–128, alone, may be sufficient for RGD-binding, since a peptide corresponding to $\beta_3$(118–128) blocks aggregation of activated platelets as well as platelet adhesion to fibrinogen. In particular, the aspartic acid residue at position 119 of $\beta_3$ appears to be required for ligand binding of the $\beta_3$(118–128) peptide because a mutation at this position renders the peptide ineffective at inhibiting platelet aggregation (D'Souza et al., Cell 79: 659–667 (1994)).

A distinct region of $\alpha_{IIb}\beta_3$ also has been implicated in RGD binding. Specifically, a synthetic peptide containing the $\beta_3$ sequence from 211–222 can inhibit binding of $\alpha_{IIb}\beta_3$ to RGD-containing ligands. This study, with those described above, indicate that there are multiple ligand contact points in $\alpha_{IIb}\beta_3$.

Thus, several lines of evidence suggest the importance of the highly conserved region spanning amino acids 109–127 of $\beta_3$, although some studies indicate that conserved residues such as $Asp^{126}$ may not be important for function. In particular, the amino-terminal segment of this conserved region appears critical since residues $Asp^{119}$, $Ser^{121}$ and $Ser^{123}$ are intolerant of mutation.

The present invention is directed to the surprising discovery that small cyclic peptides, containing only the C-terminal portion of the 109–127 region conserved among β subunits, have RGD-binding activity. The short peptide motif, (W/P)DD(G/L)(W/L)(W/L/M), which corresponds to amino acids 126–131 of $\beta_3$, is much smaller than previously described RGD-binding peptides. Unexpectedly, amino acids 119–123, which include several residues suggested to be important for the RGD-binding activity of intact integrins as described above, are not required for RGD binding activity.

The peptides of the present invention are characterized by divalent cation-independent RGD-binding activity. As used herein, the term "divalent cation-independent" refers to RGD-binding activity which does not require divalent cations. Divalent cations are positively charged ions which have a valence of two, such as $Ca^{+2}$ and $Mg^{+2}$. Divalent cation-independent binding is to be distinguished from divalent cation-dependent binding, in which there is a requirement for micromolar or higher concentrations of calcium or magnesium, for example, as described in Example IVB.

In intact integrin receptors, ligand-binding function is dependent upon a physiological concentration of divalent cations. Furthermore, the interaction of the RGD-binding domain with its ligand is dependent upon an "activated" integrin conformation. For example, $\alpha_{IIb}\beta_3$, which is maintained in an inactive conformation on resting platelets, undergoes a measurable conformational change and becomes competent to bind ligand upon treatment with platelet activators such as thrombin. Since the conformation of $\alpha_{IIb}\beta_3$ can be modulated by micromolar or higher concentrations of $Ca^{+2}$ or $Mg^{+2}$, receptor-bound cations may be required to present the ligand recognition pocket in a conformation competent for binding.

The $\beta_3$ peptide 118–131 has been shown to possess both RGD-binding and cation-binding properties, further emphasizing the intimate relationship between ligand and cation binding for integrin function. In addition, this peptide contains a series of conserved oxygenated residues reminiscent of the $Ca^{+2}$ binding motif known as an "EF hand". The integral role of the cluster of conserved oxygenated residues $Asp^{119}$, $Ser^{121}$, $Ser^{123}$, $Asp^{126}$, $Asp^{127}$ and $Ser^{130}$ within this region is supported, for example, by loss of RGD-binding activity in $Asp^{119}$, $Ser^{121}$ or $Ser^{123}$ mutants. The conservation of the $Ca^{+2}$ binding EF hand motif and the demonstrated functional importance of several oxygenated residues in $\beta_3$(118–131) implies that a functional calcium-binding motif is required for RGD binding activity.

The present invention is directed to the surprising discovery that divalent cations are not required for the binding of the cyclic peptides of the invention to RGD-containing ligands. As discussed above, a body of evidence supports the divalent cation requirement in intact integrins. Furthermore, the presence of a $Ca^{+2}$ binding "EF hand" motif in a peptide with RGD-binding activity also suggested the importance of divalent cations for RGD-binding. In contrast with what was believed by those skilled in the art, the present invention provides novel cyclic peptides capable of binding to RGD in the absence of divalent cations.

Cyclic peptides of the present invention are useful for identifying and isolating novel integrin ligands in solid phase assays. In such solid phase assays, the cyclic peptides of the invention are immobilized on a solid support. Such peptides, which have divalent cation-independent RGD-binding activity, are preferred for use in solid phase assays as compared to longer linear RGD-binding peptides, which must first fold and assume a cation binding conformation prior to binding ligand. Such a conformation can be hindered by the solid support. Similarly, the cyclic peptides of the invention can be useful for identifying novel molecules that reduce or inhibit the binding of RGD-containing ligands to integrins. In such an assay, the binding of cyclic peptides of the invention and known RGD-containing ligands would be assayed to determine whether a molecule could reduce or inhibit binding.

Specific cyclic peptides of the present invention can be isolated by a variety of methods based on their RGD-binding activity. For example, peptides characterized by specific RGD-binding activity may be identified by screening a large collection, or library, of random cyclic peptides or cyclic peptides of interest. Cyclic peptide libraries include, for example, tagged chemical libraries comprising peptides and peptidomimetic molecules. Cyclic peptide libraries also comprise those generated by phage display technology. Phage display technology includes the expression of peptide molecules on the surface of phage as well as other methodologies by which a protein ligand is or can be associated with its encoding nucleic acid. Methods for the production of phage display libraries, including vectors and methods of diversifying the population of peptides which are expressed, are well known in the art. (See, for example, Smith and Scott, *Methods Enzymol.* 217: 228–257 (1993); Scott and Smith, *Science* 249: 386–390 (1990); and Huse, WO 91/07141 and WO 91/07149, each of which is incorporated herein by reference; see, also, Example I). Cyclic peptide libraries also are well known in the art (see, for example, Koivunen et al., Methods Enzymol. 245: 346–369 (1994)). These or other well known methods can be used to produce a phage display library, from which peptides of the invention can be isolated using a variety of assays for RGD-binding activity. Other methods for producing RGD-binding cyclic peptides include, for example, rational design and mutagenesis.

RGD-binding assays are well known in the art. Such well known binding assays include ELISA and radioreceptor assays. A cyclic peptide library can be screened for RGD-binding activity using any one of a number of RGD-containing ligands. RGD-binding activity can be assayed, for example, using native RGD-containing proteins such as vitronectin and fibronectin as demonstrated in Example III. Protein fragments retaining at least one RGD sequence, such as the $10^{th}$ type III repeat of fibronectin, or RGD-containing peptides also can be used as ligands to assay RGD-binding activity (see Example I). As discussed above, RGD-containing peptides encompass anti-$\alpha_{IIb}\beta_3$ monoclonal antibodies that contain an RYD sequence as a functional equivalent of RGD. Such monoclonal antibodies, for example PAC1, OPG2 and LJ-CP3 which are well known in the art, similarly can be used to screen peptide libraries for RGD-binding peptides. Furthermore, specific RGD-binding can be distinguished from non-specific binding by the inclusion of appropriate controls, such as a non-RGD-containing fibronectin fragment or an unrelated protein such as bovine serum albumin (see Example I).

The peptides of the present invention can be isolated or synthesized using methods well known in the art. Such methods include recombinant DNA methods and chemical synthesis. Recombinant methods of producing a peptide through expression of a nucleic acid sequence encoding a peptide in a suitable host cell are well known in the art, such as is described in Sambrook et al., *Molecular Cloning: A Laboratory Manual*, 2nd Ed, Vols 1 to 3, Cold Spring Harbor, N.Y. (1989), which is incorporated herein by reference.

Peptides of the invention can also be produced by chemical synthesis, for example, by the solid phase peptide synthesis of Merrifield (Merrifield et al., *J. Am. Chem. Soc.*, 85:2149 (1964), which is incorporated herein by reference). Standard solution methods well known in the art also can be used to synthesize a peptide of the present invention (see, for example, Bodanszky, M., *Principles of Peptide Synthesis* (Springer-Verlag, 1984), which is incorporated herein by reference). Newly synthesized peptides can be purified, for example, by high performance liquid chromatography (HPLC), and can be characterized using, for example, mass spectrometry or amino acid sequence analysis. Methods exemplifying the synthesis and purification of peptides are provided in Example IIA.

A newly synthesized linear peptide can be cyclized by the formation of a bond between reactive amino acid side chains. For example, a peptide containing a cysteine-pair, or any of the cysteine analogs shown in Table 1, can be synthesized, and a disulfide bridge can be formed by oxidizing the peptide with 0.01 M $K_3[Fe(CN)_6]$ at pH 8.4, as described in Example IIA. Alternatively, a lactam, a lysinonorleucine or a dityrosine bond can be formed. Methods for forming these and other bonds are well known in the art and are based on well established principles of chemical reactivity (Morrison and Boyd, *Organic Chemistry*, 6th Ed. (Prentice Hall, 1992), which is incorporated herein by reference).

A peptide of the present invention also can be cyclized by forming a peptide bond between non-adjacent amino acid residues as described, for example, by Schiller et al., *Int. J. Pept. Prot. Res.* 25:171 (1985), which is incorporated herein by reference. Peptides can be synthesized on the Merrifield resin by assembling the linear peptide chain using $N^\alpha$-Fmoc-amino acids and Boc and tertiary-butyl proteins. Following release of the peptide from the resin, a peptide bond can be formed between the amino and carboxyl termini.

In another embodiment, the present invention provides an antibody selectively reactive with a cyclic peptide containing the sequence (W/P)DD(G/L)(W/L)(W/L/M). An antibody raised against a cyclic RGD-binding peptide of the invention can be useful for detecting multiple integrin $\beta$ subunits in various applications.

As used herein, the term "selectively reactive" refers to an antibody which can distinguish, or can be made to distinguish, related sequences over unrelated sequences. The term related sequences as used herein includes identical peptide or protein sequences as well as different but similar peptide or protein sequences. Thus, antibodies selectively reactive with a peptide of the invention will react with sequences which include, for example, CWDDGWLC (SEQ. ID. NO. 1) and CWDDLWWLC (SEQ. ID. NO. 2). Such antibodies also can react with the integrin $\beta_3$ subunit, or related $\beta$ subunits, which contain the sequence DDLW or DDL.

As used herein, the term "antibody" refers to polyclonal and monoclonal antibodies, as well as polypeptide fragments of antibodies that retain selective reactivity for a peptide of the invention. One skilled in the art would know that antibody fragments such as Fab, F(ab')$_2$ and Fv fragments can retain selective reactivity for cyclic peptides of the invention and, thus, are included within the definition of an antibody. In addition, the term "antibody" as used herein includes naturally occurring antibodies as well as non-naturally occurring antibodies and fragments that retain binding activity. Such non-naturally occurring antibodies can be constructed using solid phase peptide synthesis, produced recombinantly or obtained, for example, by screening combinatorial libraries consisting of variable heavy chains and variable light chains as described by Huse et al., *Science* 246:1275–1281 (1989), which is incorporated herein by reference.

Particularly useful non-naturally occurring antibodies include chimeric antibodies and humanized antibodies. Chimeric antibodies and humanized antibodies are useful for administration to a human subject, since the likelihood of an immune response by the subject against the antibody is minimized.

Methods for producing an antibody are routine in the art as described, for example, by Harlow and Lane, *Antibodies: A Laboratory Manual* (Cold Spring Harbor Laboratory Press, 1988), which is incorporated herein by reference. One skilled in the art would know that a cyclic peptide useful as an immunogen can be produced recombinantly or can be chemically synthesized, as described in detail above. In some cases, a cyclic peptide of the invention can be made more immunogenic by coupling the hapten to a carrier molecule such as bovine serum albumin or keyhole limpet hemocyanin. In addition, various other carrier molecules and methods for coupling a hapten to a carrier molecule are well known in the art (see, for example, Harlow and Lane, supra, 1988).

Polyclonal antibodies selectively reactive with a cyclic peptide of the invention can be raised in rabbits for example. In addition, monoclonal antibodies can be obtained using known methods (Harlow and Lane, supra, 1988). Similarly, methods for identifying an antibody selectively reactive with a cyclic peptide of the invention are known in the art and include, for example, enzyme-linked immunosorbent assays, radioimmunoassays and precipitin assays (Harlow and Lane, supra, 1988; chap. 14).

In another embodiment, peptides of the present invention are used to reduce or inhibit integrin-mediated cell attachment to an RGD-containing ligand by administering an effective amount of the RGD-binding peptide. The RGD-containing ligand can be an extracellular matrix protein, for example, such as vitronectin, fibronectin, osteopontin or fibrinogen.

As used herein, the term "cell attachment" is meant to include the attachment of cells to other cells and to RGD-containing ligands such as extracellular matrix proteins and certain viruses. Platelet aggregation is an example of cell attachment, as is the attachment of cells to insoluble substrates such as fibronectin or vitronectin. The term cell attachment encompasses the attachment of cells in vitro and in vivo. Assays to measure cell attachment are well known in the art and are described in Example III.

As used herein, the term "effective amount" means the amount of a peptide useful for reducing or inhibiting cell attachment in vitro or in vivo. An effective amount for reducing or inhibiting cell attachment can be determined using methods known to those in the art, including the assay described in Example III.

Peptides of the present invention are useful in modulating the activity of RGD-binding integrins such as $\alpha_5\beta_1$, $\alpha_{IIb}\beta_3$ and $\alpha_v\beta_3$ due to the ability of the claimed peptides to reduce or inhibit cell attachment by binding RGD-containing ligands. Inhibition of cell attachment by peptides of the invention is useful in the treatment of pathologies resulting from abnormal integrin-mediated cell attachment, such as thrombosis, osteoporosis, inflammation, tumor growth or metastasis. Unlike currently available RGD-containing peptides, which target the cell carrying the RGD-binding integrin, peptides of the present invention target the integrin ligand. Since the binding of an RGD-containing peptide to an integrin has been shown to be capable of inducing signaling by the integrin, peptides of the present invention, which bind to a different target, add a useful alternative to the compounds currently available for inhibition of cell attachment.

Thus, cyclic peptides of the invention can reduce or inhibit the binding of platelets to fibrinogen by administration of a sufficient quantity of peptide to the cells. The reduction or inhibition of integrin binding to fibrinogen is useful, for example, in the treatment of thrombosis, since $\alpha_{IIb}\beta_3$ mediates platelet aggregation. Peptides of the invention also can reduce or inhibit infection by several types of viruses that use an RGD-containing protein to gain entry to host cells. Such viruses include, for example, hoof-and-mouth viruses and certain adenoviruses. Similarly, the cyclic RGD-binding peptides of the invention can be useful in inhibiting or reducing the severity of other pathologies resulting from abnormal integrin-mediated cell attachment.

EXAMPLE I

IDENTIFICATION OF RGD-BINDING PEPTIDES

This example describes isolation of peptides of the invention.

A. Isolation of Phage Capable of Binding to Fibronectin Fragments

To isolate peptides that interact with the RGD-containing 10th type III domain of fibronectin ($III_{10}$), recombinant fibronectin fragments were used to select clones from a mixture of peptide libraries by successive rounds of affinity panning and elution with RGD-containing peptide. Phage display libraries were made as described (Koivunen et al., *Methods Enzymol.* 245:346–369 (1994), which is incorporated herein by reference) using the fuse 5 vector (Smith and Scott, *Methods Enzymol.* 217: 228–257 (1993), which is incorporated herein by reference). Mixtures of libraries displaying $CX_5C$, $CX_6C$, $CX_7C$ and $CX_9$ (wherein $X_5$, $X_6$, $X_7$ and $X_9$ represent a sequence of 5, 6, 7 or 9, respectively, randomly selected amino acids) peptides were screened for binding to fibronectin fragments coated on microtiter wells.

The fibronectin fragments used to coat the wells were prepared as follows. Human plasma fibronectin was from the Finnish Red Cross (Helsinki, Finland). A 110-kD fragment of fibronectin was prepared as described previously in Pierschbacher et al., *Cell* 26: 259–267 (1981) which is incorporated herein by reference. Recombinant fibronectin fragments containing type III repeats 8 and 9, 9 and 10, 10 and 11, 10 alone, and 8 through 11 were produced as described (Dickinson et al., *J. Mol. Biol.* 238: 123–127 (1994), which is incorporated herein by reference), using the GST protein fusion system (Pharmacia, Uppsala, Sweden) for the 8 through 11 fragment and the His-Tag fusion protein system (Qiagen, Chatsworth, Calif.) for the other four fragments. A fragment encompassing the alternatively spliced cell attachment domain of fibronectin, which comprises amino acids 1860–2140, was also produced using the His-Tag system.

Panning was performed on each fragment individually. In the first and second rounds of panning, the coating concentration of protein was 5 µg/well. To increase the stringency of the panning, the wells were coated with decreasing concentrations of protein: 1.0 µg/well and 0.1 µg/well. Phage were selected for further amplification from the well with the lowest protein concentration that showed phage binding over background, where binding was detected and quantified by infection of bacteria. In the fourth panning, the concentration of fibronectin fragment was 10 ng/well. To recover the bound phage, the wells were eluted with a 1 mM solution of GRGDSP (SEQ. ID. NO. 15) or CELRGDGWC (SEQ. ID. NO. 16) peptides, 2 mM EDTA or were directly incubated with 50 µl of bacteria. Phage were sequenced from randomly selected clones as described in Koivunen et al., *Methods Enzymol.* 245: 346–369 (1994).

Decreasing protein coating concentration in the second and third rounds of panning, and the use of an excess of phage to introduce binding competition, allowed for selection of specific phage that bound with high-affinity to the fibronectin fragments. In the third round of panning, 50- to 150-fold enrichment was achieved on $III_{10}$-bearing fragments. The fragment containing the $10^{th}$ and $11^{th}$ type III repeats of fibronectin was the most efficient binder of specific phage. Enrichment was also seen on the recombinant fibronectin fragment bearing the $III_{10}$ domain alone, but not on the fragment from the alternatively spliced fibronectin domain containing the CS-1 binding site for $\beta_4\beta_1$ integrin (results not shown). Binding of phage to fragment $III_{8,9}$ was also low, indicating that the $III_{10}$ domain was important for the enrichment of RGD-eluted phage. Glutathione S transferase (GST) and bovine serum albumen (BSA) were used as controls for non-specific attachment and showed negligible phage binding. Enrichment of specific phage was also seen with the RGD-coating fragments when the phage were eluted with EDTA or collected by direct infection of bacteria added to the washed wells.

B. Phagre Selected by RGD-containing Fibronectin Fragments Display the (W/P)DD(G/L)(W/L)(W/L/M) Peptide Motif Sequences of the insert in the phage eluted with RGD peptides, EDTA, or recovered by direct incubation of bacteria showed that approximately 80–85% of the clones displayed the motif CWDDGWLC (SEQ. ID. NO. 1) (see Table 2 above). Furthermore, the CWDDGWLC (SEQ. ID. NO. 1) sequence was not encoded by a single clone, since there was variation at the nucleotide level among the phage.

Some of the other motifs found were similar to the CWDDGWLC (SEQ. ID. NO. 1) sequence: the glycine residue in the fifth position was frequently replaced by leucine. In addition, the tryptophan in the second position could be replaced by proline; the tryptophan in the sixth position could be replaced by leucine; and the leucine in the seventh position could be replaced by tryptophan or methionine.

The sequences that were not related to the (W/P)DD(G/L)(W/L)(W/L/M) motif were hydrophobic and/or were seen only once. The binding of these phage is likely to have been non-specific. These rarely isolated peptides were lost in the subsequent high affinity screening steps and were not seen at all when specific elution with an RGD peptide was used.

EXAMPLE II

ASSAYS FOR RGD-BINDING ACTIVITY

This example describes specific RGD-binding assays for the analysis of phage displaying peptides and for the analysis of synthetic peptides.

A. Binding of CWDDGWLC Phage to the Fibronectin $III_{10}$ Domain is Blocked with Synthetic Peptides The specificity of the CWDDGWLC-phage (SEQ. ID. NO. 1) binding to fibronectin and fibronectin fragments was tested in a microtiter assay.

The phage attachment assay was performed by binding individual cloned phage to insolubilized fibronectin or fibronectin fragments in microtiter assays as described (Koivunen et al., *Methods Enzymol.* 245: 346–369 (1994) and Koivunen et al., *J. Cell Biol.* 124: 373–380 (1994), which are each incorporated herein by reference). The coating concentration for the proteins was 10 μg/ml. Coating with peptides was carried out at 10–100 μg/ml overnight with or without 1 mM divalent cations. Phage binding was determined by growing K91kan bacteria in the presence of the selection marker tetracycline. The absorbance at 600 nm was read after 16–24 hours of incubation at room temperature (Koivunen et al., *Methods Enzymol.* 245: 346–369 (1994)). Alternatively, phage binding was quantified using sheep anti-M13 polyclonal antibodies (1 μg/ml; Pharmacia). Readings at 450 nm were analyzed after incubation with alkaline phosphatase conjugated anti-sheep IgG (1:10,000; Sigma).

The binding was dependent on the presence of the $III_{10}$ domain. Binding to $III_{8,9}$, to control proteins (BSA and GST) and also to the fragment encompassing the alternatively spliced cell attachment domain of fibronectin was minimal. An unrelated phage displaying the peptide CRDPRAODLC (SEQ. ID. NO. 17) showed no binding to fibronectin or any of its fragments.

Two cyclic peptides, CWDDGWLC (SEQ. ID. NO. 1) and ACRGDGWMCG (SEQ. ID. NO. 18), were synthesized and tested for their ability to inhibit phage binding to the $III_{8,11}$ fragment. Peptides were synthesized on a synthesizer (Model 430A: Applied Biosystems, Foster City, Calif.) by standard Merrifield solid phase synthesis protocols and t-butoxycarbonyl chemistry. Cyclic peptides were prepared by oxidizing with 0.01M $K_3Fe(CN)_6$ at pH 8.4 overnight and purified by reverse-phase HPLC. The peptide structures were confirmed by mass spectroscopy. Both peptides, but not an irrelevant cyclic one (i.e., GACVRLNSLACGA) (SEQ. ID. NO. 19), inhibited CWDDGWLC-phage (SEQ. ID. NO. 1) binding in a dose-dependent manner. EDTA did not inhibit the binding of CWDDGWLC-phage (SEQ. ID. NO. 1), although CWDDGWLC-phage (SEQ. ID. NO. 1) were detected in the EDTA eluates after affinity panning. The recovery of the CWDDGWLC-phage (SEQ. ID. NO. 1) with EDTA, (Table 2), may have represented non-specific release of the bound phage rather than specific elution, because fewer phage were eluted with EDTA than with the RGD peptide.

Therefore, binding of the CWDDGWLC (SEQ. ID. NO. 1) phage to the RGD-containing fibronectin fragments was specific because only background binding was seen when fragments lacking the RGD-containing $III_{10}$ domain, or control proteins, were used. Moreover, the specificity of the CWDDGWLC-phage (SEQ. ID. NO. 1) binding to fibronectin fragments also was supported by specific inhibition of the interaction by peptides representing the motif itself and by RGD-containing peptides.

B. Phage Attachment to Immobilized Peptides

The binding of CWDDGWLC (SEQ. ID. NO. 1) and RGD-displaying phage to RGD and CWDDGWLC-containing (SEQ. ID. NO. 1) peptides was analyzed in phage attachment assays using CWDDGWLC (SEQ. ID. NO. 1), A CRGDGWMCG (SEQ. ID. NO. 18), and an irrelevant cyclic peptide GACVRLNSLACGA (SEQ. ID. NO. 19) as substrates. RGD- and CWDDGWLC (SEQ. ID. NO. 1) containing cyclic peptides were coated on microtiter wells at 20 μg/ml and used to bind phage. Soluble peptides were added at 1 mM concentration. CWDDGWLC-phage (SEQ. ID. NO. 1) bound to immobilized RGD-containing peptide.

Conversely, RGD-phage, i.e., phage displaying a peptide containing the CELRGDGWC motif (SEQ. ID. NO. 16), bound to immobilized CWDDGWLC (SEQ. ID. NO. 1). The RGD phage also showed slight, but consistent, binding to the peptide displaying the same RGD motif, RGDGW. Addition of either the CWDDGWLC (SEQ. ID. NO. 1) or ACRGDGWMCG (SEQ. ID. NO. 18) peptide in solution blocked the CWDDGWLC-phage (SEQ. ID. NO. 1) binding, whereas an unrelated peptide had no effect. The binding of RGD-phage was also inhibited by both peptides, but was unaffected by control peptide or by EDTA.

C. Fibronectin Binds to CWDDGWLC-sepharose

Affinity chromatography showed that fibronectin bound to CWDDGWLC-Sepharose (SEQ. ID. NO. 1). Peptides were coupled to Sepharose-CH (Pharmacia) according to manufacturer's instructions. Fibronectin or fibronectin fragments at 2 mg/ml in TBS were applied to CWDDGWLC-Sepharose (SEQ. ID. NO. 1). After extensive washing with TBS, bound fibronectin was eluted with the GRGDSP (SEQ. ID. NO. 15) peptide (1 mM) but not with the GRGESP (SEQ. ID. NO. 21) peptide (1 mM), as determined by analysis of eluate samples by SDS-PAGE followed by Coomassie blue staining. Fibronectin was not retained in a control unrelated peptide column. Fibronectin fragments lacking the $III_{10}$ domain (i.e., fragment $III_{8,9}$) and unrelated proteins (BSA and type IV collagen) were not retained in the CWDDGWLC-Sepharose (SEQ. ID. NO. 1) column, as determined by analysis of fractions eluted in glycine/NaCl (pH 3.0) for protein by measuring OD280.

EXAMPLE III

CELL ATTACHMENT ASSAY

This example describes an assay for peptide inhibition of the cell attachment function of integrins.

A. CWDDGWLC Inhibits RGD-dependent Cell Adhesion

CWDDGWLC (SEQ. ID. NO. 1) peptide inhibition of integrin function was assayed in cell attachment assays with the osteosarcoma cell line, MG-63 which attaches to fibronectin, vitronectin, and collagens through its complement of several integrins (Pytela et al., *Methods Enzymol.* 144: 475–489 (1987)). Microtiter wells were coated with fibronectin, vitronectin or type IV collagen at concentrations that resulted in 60% of maximal attachment (~5 μg/ml). Human plasma fibronectin was from the Finnish Red Cross (Helsinki, Finland). Vitronectin was purified from human plasma as described in Yatohgo et al., *Cell Struc. Funct.* 13: 281–292 (1988), which is herein incorporated by reference. Collagen was from Collaborative Research (Bedford, Mass.). Free binding sites on plastic were blocked with BSA. Approximately $1 \times 10^5$ cells per well were allowed to attach for 30 min in the presence or absence of competing peptides and the bound cells were quantitated by staining with crystal violet (Morla et al., *Nature* 367: 193–196 (1994)).

The CWDDGWLC (SEQ. ID. NO. 1) peptide inhibited cell adhesion when either fibronectin or vitronectin were used as substrates, but not on collagen type IV. An unrelated cyclic peptide had no effect on any of the substrates. The peptide CWDDGWLC (SEQ. ID. NO. 1) was slightly less effective than the standard RGD peptide, GRGDSP (SEQ. ID. NO. 15).

EXAMPLE IV

STRUCTURAL SIMILARITY TO THE β3-INTEGRIN SUBUNIT

This example provides a method for the production of antibodies against the CWDDGWLC (SEQ. ID. NO. 1)

peptide. This example further describes a method for analyzing the structural relationship between the cyclic CWDDGWLC (SEQ. ID. NO. 1) peptide and integrin β subunits.

A. *CWDD$^G$/$_L$WLC* Resembles a Peptide from β3 Integrin Subunit

A DDLW sequence from the ligand binding region of the β subunits shows similarity to the RGD binding peptides of the invention (see Table 3). A synthetic peptide containing the DDLW sequence of the β3 subunit (amino acids 109–133; DYPVDIYYLMDLSYSMKDDLWSIQN (SEQ. ID. NO. 23)) has been shown to bind to an RGD peptide (D'Souza et al., Cell 79: 659–667 (1994)). As shown in FIG. 1, RGD-phage bound to the β3(109–133) peptide (SEQ. ID. NO. 23).

TABLE 3

COMPARISON OF THE RGD-BINDING SEQUENCE
FROM PEPTIDE LIBRARY WITH INTEGRIN SEQUENCES

CWDDG/LWLC

β3: DIYYLM<u>D</u>LSYSMK<u>DD</u>LWSIQNLGTKLAT (SEQ. ID. NO 25)

β1: DLYYLMDLSYSMKDDLENVKSLGTDLMN (SEQ. ID. NO 26)

β5: DLYYLMDLSLSMKDDLDNIRSLGTKLAEE (SEQ. ID. NO 27)

β6: DLYYLMDLSAAMDDDLNTIKELGSGLSKE (SEQ. ID. NO 28)

The amino acid sequences of integrin β subunits are shown using the single-letter code. The sequence of β3 that is shown encompasses residues 113–140. Residues $D^{119}$, $D^{126}$, and $D^{127}$ within the β3 subunit are underlined.

Figure 1B:
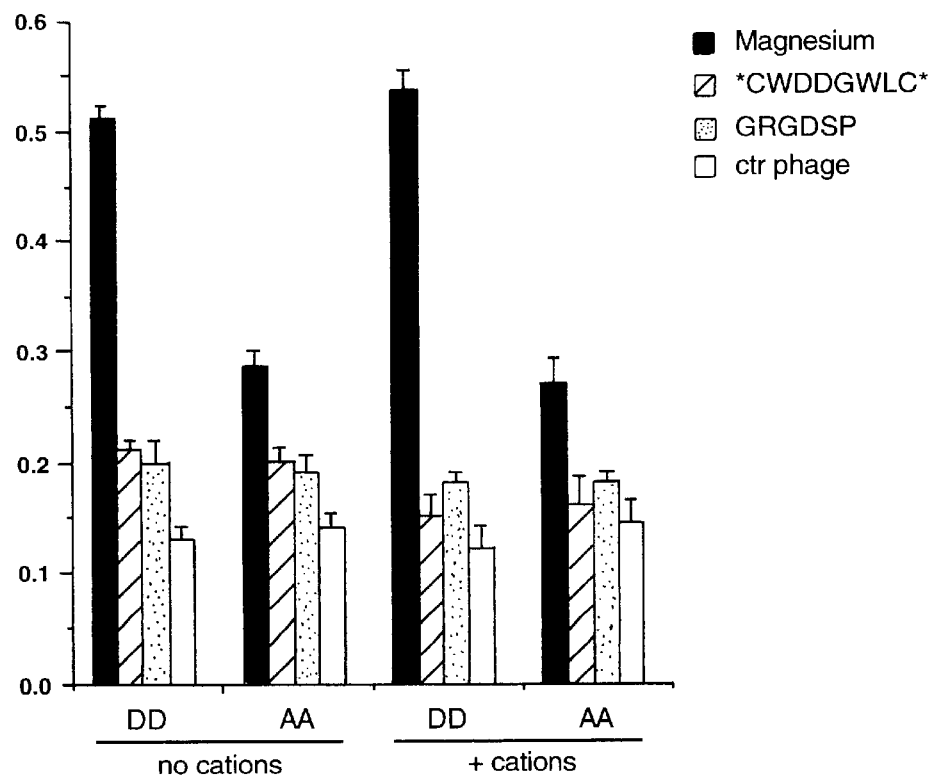

The binding required the presence of divalent cations, either while the peptide was coated onto plastic or during the phage binding (FIG. 1a). The binding of the RGD-phage was blocked by addition of soluble CWDDGWLC (SEQ. ID. NO. 1) or GRGDSP (SEQ. ID. NO. 15) peptides (FIG. 1b). The two peptides were equally effective in inhibiting RGD-binding to β3(109–133) (SEQ. ID. NO. 23): In titration experiments, 50% inhibition was achieved at about 1 μM concentration of the peptides (not shown). However, EDTA did not block phage binding when peptides were allowed to coat in the presence of cations.

To establish whether the DDLW sequence in the β3(109–133) peptide (SEQ. ID. NO. 23) was important for the RGD-phage binding, we synthesized a variant β3 peptide in which the aspartate residues at positions 126 and 127 were replaced by alanines (DYPVDIYYLMDLSYSMKAALWSIQN (SEQ. ID. NO. 24) designated "AA"). RGD-phage binding to this "AA" variant (SEQ. ID. NO. 24) was much weaker than to the wild type peptide (FIG. 1), indicating an important role for the two aspartate residues in the interaction. The residual binding to the "AA" peptide (SEQ. ID. NO. 24) had the same cation requirements as the binding to the wild type peptide.

B. Antibodies against CWDDGWLC Peptide Recognize β3 and β1 in Immunoblots

Further evidence for the structural similarity between CWDDGWLC (SEQ. ID. NO. 1) and β subunits was obtained with antibodies raised against CWDDGWLC (SEQ. ID. NO. 1), whose preparation is described below. When purified $α_{IIb}β_3$ was probed in immunoblots with anti-CWDDGWLC (SEQ. ID. NO 1), a band was detected that had the expected molecular size of β3 and aligned with the band detected by anti-β3 cytoplasmic domain antiserum. Reactivity of the anti-CWDDGWLC (SEQ. ID. NO 1) serum could be abrogated by preincubation of the serum with either CWDDGWLC (SEQ. ID. NO. 1) or β3(109–133) peptide (SEQ. ID. NO. 23). The anti-CWDDGWLC (SEQ. ID. NO 1) serum also reacted with bands that co-migrated with β1 and β3 subunits in MG-63 total cell extracts. Anti-β1 monoclonal antibody TS2/16 against β1 was used as a positive control. The reactivity of anti-CWDDGWLC (SEQ. ID. NO 1) serum was abrogated by pre-incubation of the antiserum with either CWDDGWLC (SEQ. ID. NO. 1) or β3(109–133) (SEQ. ID. NO. 23). As expected, these peptides had no effect on the reactivity of the positive control antibodies in a or b.

Immunization was performed as follows. RBF-Dnj mice (Jackson Laboratories, Bar Harbor, Me.) were immunized with 200 μg CWDDGWLC (SEQ. ID. NO. 1) peptide coupled to sheep red blood cells (Sigma) by intraperitoneal injection every 15 days for 3 months according to the manufacturer's instructions.

Immunoblot analysis of anti-CWDDGWLC (SEQ. ID. NO. 1) antiserum was performed as follows. Purified $α_{IIb}β_3$ (2 μg/lane) and MG-63 cell extracts (20 μl from a vol/vol detergent/cell pellet solution) were separated on 4–12% gradient SDS-PAGE and transferred to Immobilon-P membranes. After blocking of non-specific sites, filters were probed with anti-CWDDGWLC (SEQ. ID. NO. 1) at a 1:500 dilution and anti-β3 cytoplasmic domain polyclonal serum at a 1:2,000 dilution. MG-63 osteosarcoma cell extracts also were probed with TS2/16 (10 μg/ml), which is an anti-β1 monoclonal antibody. Normal mouse and rabbit sera were used as negative controls. To confirm specificity of the serum, filters were incubated with anti-CWDDGWLC (SEQ. ID. NO. 1) serum in the presence of 100 μM of the CWDDGWLC (SEQ. ID. NO. 1) or the β3(119–133) (SEQ. ID. NO. 23) peptides in solution.

Purified $α_{IIb}β_3$ was from Enzyme Research Laboratories Inc. (South Bend, Ind.). Anti-β1 monoclonal antibody TS2/16 was provided by Dr. Martin Hemler (Dana Farber Cancer Institute, Harvard Medical School, Boston, Mass.). Reactivity of antibodies was detected with anti-mouse or rabbit IgG, and chemiluminescence (ECL; Amersham).

Although the invention has been described with reference to the examples provided above, it should be understood that various modifications can be made without departing from the spirit of the invention. Accordingly, the invention is limited only by the claims.

We claim:

1. A compound having RGD-binding activity, comprising a cyclic peptide coupled to a moiety,
    wherein said cyclic peptide has the amino acid sequence:
    $X_1X_2DDX_4X_5X_7X_8$ (SEQ. ID. NO 20),
    wherein
    $X_1$ and $X_8$ each is an independently selected amino acid;
    $X_2$ and $X_7$ together equal 0 to 4 amino acids, each amino acid of which is independently selected;
    $X_4$ is selected from the group consisting of glycine and leucine; and
    $X_5$ is selected from the group consisting of tryptophan and leucine
    and wherein said moiety is selected from the group consisting of a phage, polypeptide, carrier molecule, solid support and chemical molecule.

2. The compound of claim 1, wherein $X_1$ and $X_8$ each is independently selected from the group consisting of cysteine; penicillamine; β,β-pentamethylene-β-mercaptopropionic acid; β,β-pentamethylene cysteine and functional equivalents thereof.

3. The compound of claim 1, wherein $X_1$ and $X_8$ each is cysteine.

4. The compound of claim 2, wherein $X_4$ is glycine and $X_5$ is tryptophan.

5. The compound of claim 1, wherein said RGD-binding activity is divalent cation-independent.

6. The compound of claim 1, wherein said moiety is a phage.

7. The compound of claim 1, wherein said moiety is a polypeptide.

8. The compound of claim 1, which is a fusion protein.

9. A compound having RGD-binding activity, comprising a cyclic peptide coupled to a moiety, wherein said cyclic peptide has the amino acid sequence:
    $X_1X_2X_3DDX_4X_5X_6X_7X_8$ (SEQ. ID. NO 22),
    wherein
    $X_1$ and $X_8$ each is an independently selected amino acid;
    $X_2$ and $X_7$ together equal 0 to 3 amino acids, each amino acid of which is independently selected;
    $X_3$ is selected from the group consisting of tryptophan and proline;
    $X_4$ is selected from the group consisting of glycine and leucine;
    $X_5$ is selected from the group consisting of tryptophan and leucine; and
    $X_6$ is selected from the group consisting of leucine, tryptophan and methionine
    and wherein said moiety is selected from the group consisting of a phage, polypeptide, carrier molecule, solid support and chemical molecule.

10. The compound of claim 9, wherein $X_1$ and $X_8$ each is independently selected from the group consisting of cysteine; penicillamine; β,β-pentamethylene-β-mercaptopropionic acid; β,β-pentamethylene cysteine and functional equivalents thereof.

11. The compound of claim 10, wherein $X_1$ and $X_8$ each is cysteine.

12. The compound of claim 9, wherein said RGD-binding activity is divalent cation-independent.

13. The compound of claim 9, wherein said moiety is a phage.

14. The compound of claim 9, wherein said moiety is a polypeptide.

15. The compound of claim 14, which is a fusion protein.

16. The compound of claim 1, wherein said moiety is a carrier molecule.

17. The compound of claim 1, wherein said moiety is a solid support.

18. The compound of claim 1, wherein said moiety is a chemical molecule.

19. The compound of claim 9, wherein said moiety is a carrier molecule.

20. The compound of claim 9, wherein said moiety is a solid support.

21. The compound of claim 9, wherein said moiety is a chemical molecule.

* * * * *